(12) United States Patent
Ito et al.

(10) Patent No.: US 9,612,201 B2
(45) Date of Patent: Apr. 4, 2017

(54) SURFACE-ENHANCED RAMAN SCATTERING ELEMENT

(71) Applicant: HAMAMATSU PHOTONICS K.K., Hamamatsu-shi, Shizuoka (JP)

(72) Inventors: Masashi Ito, Hamamatsu (JP); Katsumi Shibayama, Hamamatsu (JP); Masaki Hirose, Hamamatsu (JP); Yoshihiro Maruyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/420,458

(22) PCT Filed: Aug. 9, 2013

(86) PCT No.: PCT/JP2013/071701
§ 371 (c)(1),
(2) Date: Feb. 9, 2015

(87) PCT Pub. No.: WO2014/025032
PCT Pub. Date: Feb. 13, 2014

(65) Prior Publication Data
US 2015/0212001 A1 Jul. 30, 2015

(30) Foreign Application Priority Data

Aug. 10, 2012 (JP) .................. 2012-178778

(51) Int. Cl.
*G01N 21/65* (2006.01)
*G01N 21/03* (2006.01)
*B82Y 40/00* (2011.01)

(52) U.S. Cl.
CPC ........... *G01N 21/658* (2013.01); *G01N 21/03* (2013.01); *B82Y 40/00* (2013.01); *G01N 2201/068* (2013.01)

(58) Field of Classification Search
CPC .................................................. G01N 21/658
See application file for complete search history.

(56) References Cited

U.S. PATENT DOCUMENTS

| | | | |
|---|---|---|---|
| 2004/0023046 A1 | 2/2004 | Schlottig et al. | |
| 2006/0119250 A1* | 6/2006 | Suehiro ................ | B60Q 1/2696 |
| | | | 313/498 |

(Continued)

FOREIGN PATENT DOCUMENTS

| | | |
|---|---|---|
| CN | 101024483 | 8/2007 |
| CN | 101281133 | 10/2008 |

(Continued)

OTHER PUBLICATIONS

"Q-SERS™ G1 Substrate," Opto Science, Inc. (retrieved on-line on Jul. 5, 2013).

(Continued)

*Primary Examiner* — Kara E Geisel
*Assistant Examiner* — Shawn Decenzo
(74) *Attorney, Agent, or Firm* — Drinker Biddle & Reath LLP

(57) ABSTRACT

A surface-enhanced Raman scattering element comprises a substrate having a principal surface; a molded layer having a support part formed on the principal surface of the substrate so as to extend along the principal surface and a fine structure part formed on the support part; and a conductor layer formed on the fine structure part and constituting an optical functional part for generating surface-enhanced Raman scattering; the molded layer being relatively thinner in a direction intersecting the principal surface of the substrate at an outer edge part of a fine structure area formed with the fine structure part in the molded layer than at a center part of the fine structure area.

6 Claims, 10 Drawing Sheets

(56) References Cited

U.S. PATENT DOCUMENTS

| | | | |
|---|---|---|---|
| 2006/0146323 | A1 | 7/2006 | Bratkovski et al. |
| 2007/0140900 | A1 | 6/2007 | Wang et al. |
| 2008/0094621 | A1 | 4/2008 | Li et al. |
| 2008/0142822 | A1* | 6/2008 | Kim ................. H01L 33/54 257/98 |
| 2008/0218761 | A1 | 9/2008 | Nishikawa et al. |
| 2010/0085566 | A1* | 4/2010 | Cunningham ....... G01N 21/658 356/301 |
| 2011/0027901 | A1 | 2/2011 | Gaster et al. |
| 2011/0116089 | A1 | 5/2011 | Schmidt et al. |
| 2011/0166045 | A1 | 7/2011 | Dhawan et al. |
| 2014/0028995 | A1* | 1/2014 | Bratkovski ............ G01N 21/01 356/38 |
| 2014/0043605 | A1 | 2/2014 | Tseng et al. |

FOREIGN PATENT DOCUMENTS

| | | |
|---|---|---|
| CN | 101319994 | 12/2008 |
| CN | 101529229 | 9/2009 |
| CN | 101566571 | 10/2009 |
| CN | 101629906 | 1/2010 |
| CN | 102282094 | 12/2011 |
| CN | 102330080 | 1/2012 |
| CN | 102483354 | 5/2012 |
| JP | H05-044867 U | 6/1993 |
| JP | H07-260646 A | 10/1995 |
| JP | 2003-026232 A | 1/2003 |
| JP | 2005-337771 A | 12/2005 |
| JP | 2007-530925 A | 11/2007 |
| JP | 2007-538264 A | 12/2007 |
| JP | 2008-519254 A | 6/2008 |
| JP | 2008-196992 A | 8/2008 |
| JP | 2008-268059 A | 11/2008 |
| JP | 2009-025316 A | 2/2009 |
| JP | 2009-047623 A | 3/2009 |
| JP | 2009-103643 A | 5/2009 |
| JP | 2009-222507 A | 10/2009 |
| JP | 2009-236830 A | 10/2009 |
| JP | 2009-544967 A | 12/2009 |
| JP | 2010-506191 A | 2/2010 |
| JP | 2011-021085 | 2/2011 |
| JP | 2011-033518 A | 2/2011 |
| JP | 2011-506916 A | 3/2011 |
| JP | 2011-075348 A | 4/2011 |
| JP | 2011-107032 A | 6/2011 |
| JP | 2011-141264 | 7/2011 |
| JP | 2011-141265 A | 7/2011 |
| JP | 2011-215021 A | 10/2011 |
| JP | 2012-233707 A | 11/2012 |
| WO | WO-2007/149120 A2 | 12/2007 |
| WO | WO-2010/050203 A1 | 5/2010 |
| WO | WO-2010/090111 A1 | 8/2010 |
| WO | WO-2011/021085 A2 | 2/2011 |
| WO | WO-2011/040504 A1 | 4/2011 |
| WO | WO-2012/024006 A2 | 2/2012 |
| WO | WO 2013/015810 | 1/2013 |
| WO | WO-2014/025033 A1 | 2/2014 |
| WO | WO-2014/025034 A1 | 2/2014 |

OTHER PUBLICATIONS

Masahiro Yanagisawa, "Detection of Trace Organic Gas Using Molecular Sensor with Plasmon Antenna," Green Technology, Vo. 22, No. 6, Jun. 10, 2012, pp. 42-47, including at least partial English-language translation.

International Search Report dated Nov. 12, 2013, issued in International Application No. PCT/JP2013/071695.

International Search Report dated Nov. 5, 2013, issued in International Application No. PCT/JP2013/071696.

International Search Report dated Nov. 5, 2013, issued in International Application No. PCT/JP2013/071699.

International Search Report dated Nov. 5, 2013, issued in International Application No. PCT/JP2013/071701.

International Search Report dated Nov. 19, 2013, issued in International Application No. PCT/JP2013/071702.

International Search Report dated Nov. 12, 2013, issued in International Application No. PCT/JP2013/071703.

International Search Report dated Nov. 5, 2013, issued in International Application No. PCT/JP2013/071704.

International Search Report dated Nov. 5, 2013, issued in International Application No. PCT/JP2013/071707.

International Search Report dated Nov. 5, 2013, issued in International Application No. PCT/JP2013/071709.

International Search Report dated Apr. 28, 2014, issued in International Application No. PCT/JP2014/052927.

International Search Report dated May 13, 2014, issued in International Application No. PCT/JP2014/052928.

K. Nakamoto at al., "Arrays of Metallic Nanopillars in Holes for Plasmonic Devices", Retrieved from the Internet: URL: http://www.rsc.org/images/LOC/2011/PDFs/Papers/596_0021.pdf, Oct. 6, 2011, XP055289892.

M. Tomohiko et al., "New localized surface plasmon resonance sensor utilizing nanoimprinting technology", NSTI Nanotechnology Conference and Trade Show—NSTI Nanotech, vol. 1. May 11, 2006, p. 58-p. 61, XP009098538.

W. D. Li et al., "Three-dimensional cavity nanoantenna coupled plasmonic nanodots for ultrahigh and uniform surface-enhanced Raman scattering over large area", Optics Express, vol. 19, No. 5, Feb. 14, 2011, p. 3925-3936, XP002751299.

W. Zhang et al., "Giant and uniform fluorescence enhancement over large areas using plamonic nanadots in 3D resonant cavity nanoantenna by nanoimprinting", Nanotechnolgy, vol. 23, No. 22, May 10, 2012, p. 225301, XP020224099.

S. M. Wells et al., "Efficient disc on pillar substrates for surface enhanced Raman spectroscopy", Chemical Communications—Chemcom, vol. 47, No. 13, Jan. 1, 2011, p. 3814-p. 3816, XP055289549.

Di Zhi-gang et al., "Simulation and optimization of SERS effect in nano Ag substrates", Laser & Infrared, vol. 41, No. 8, Aug. 31, 2011, p. 850-p. 855.

U.S. Office Action dated Oct. 14, 2016 that issued in U.S. Appl. No. 14/420,510 including Double Patenting Rejections on pp. 2-14.

English Machine Translation of JP 2011-107032, Nishikawa et al., Jun. 2, 2011 as attached to U.S. Office Action dated Oct. 14, 2016 in U.S. Appl. No. 14/420,510.

\* cited by examiner

50nm

SURFACE-ENHANCED RAMAN SCATTERING ELEMENT

TECHNICAL FIELD

One aspect of the present invention relates to a surface-enhanced Raman scattering element.

BACKGROUND ART

As a conventional surface-enhanced Raman scattering element, one equipped with a minute metal structure configured to generate surface-enhanced Raman scattering (SERS) has been known (see, for example, Patent Literature 1 and Non Patent Literature 1). In such a surface-enhanced Raman scattering element, when a sample to be subjected to Raman spectroscopy is brought into contact with the minute metal structure and is irradiated with excitation light in this state, surface-enhanced Raman scattering occurs, whereby Raman scattering light enhanced by about $10^8$ times, for example, is released.

Known as an example of the above-mentioned minute metal structure is one manufactured by etching a fluorine-containing silica glass layer and a silica glass film which are sequentially stacked on a silicon substrate, so as to form a plurality of minute projections, and then forming a metal film by sputtering (see, for example, Patent Literature 2).

CITATION LIST

Patent Literature

Patent Literature 1: Japanese Patent Application Laid-Open No. 2011-33518
Patent Literature 2: Japanese Patent Application Laid-Open No. 2009-222507

Non Patent Literature

Non Patent Literature 1: "Q-SERS™ G1 Substrate", [online], Opto Science, Inc., [retrieved from the Internet on 2012 Jul. 19].

SUMMARY OF INVENTION

Technical Problem

When manufacturing the minute metal structure, the above-mentioned Patent Literature 2 forms its source minute projections by etching, but they may be formed by utilizing nanoimprinting, for example. In the latter case, releasing a replica mold for nanoimprinting from a resin layer for the minute projections may damage the minute projections contributing to surface-enhanced Raman scattering, thereby making surface-enhanced Raman scattering characteristics unstable.

In view of such circumstances, it is an object of one aspect of the present invention to provide a surface-enhanced Raman scattering element which can stabilize surface-enhanced Raman scattering characteristics.

Solution to Problem

One aspect of the present invention relates to a surface-enhanced Raman scattering element. This surface-enhanced Raman scattering element comprises a substrate having a principal surface; a molded layer having a support part formed on the principal surface of the substrate so as to extend along the principal surface and a fine structure part formed on the support part; and a conductor layer formed on the fine structure part and constituting an optical functional part for generating surface-enhanced Raman scattering; the molded layer being relatively thinner in a direction intersecting the principal surface of the substrate at an outer edge part of a fine structure area formed with the fine structure part in the molded layer than at a center part of the fine structure area.

In this surface-enhanced Raman scattering element, the molded layer has the fine structure part, on which the conductor layer is formed, so as to construct the optical function part for generating surface-enhanced Raman scattering. In particular in this surface-enhanced Raman scattering element, the molded layer is made relatively thick at the center part of the fine structure area formed with the fine structure part and relatively thin at its outer edge part, respectively. Therefore, when releasing the mold from the molded layer in order to form the molded layer by nanoimprinting, for example, the fine structure part is more likely to comply with the release of the replica mold at the outer edge part of the fine structure area and keep its form at the center part of the fine structure area. This inhibits the fine structure part from being damaged and thus can stabilize surface-enhanced Raman scattering characteristics.

In the surface-enhanced Raman scattering element in accordance with one aspect of the present invention, the fine structure part may include a plurality of projections formed on the support part, the projections having a forming density relatively lower at the center part of the fine structure area than at the outer edge part thereof. This makes it possible to form the molded layer easily and securely by nanoimprinting, for example, such that it becomes relatively thinner at the outer edge part of the fine structure area than at the center part thereof.

Here, the forming density of the projections is defined by the total volume of the projections formed within a predetermined reference area, for example. Therefore, the forming density herein becomes higher and lower when the total volume of the projections formed within the predetermined area is larger and smaller, respectively. When the projections to be compared with each other in terms of forming density have a uniform shape, for example, whether the forming density is high or low corresponds to whether the number of projections formed within the predetermined area is large or small.

In the surface-enhanced Raman, scattering element in accordance with one aspect of the present invention, the molded layer may be made relatively thinner in the direction intersecting the principal surface of the substrate at the outer edge part of the fine structure area than at the center part of the fine structure area due to a gradient in thickness of the support part. This can also form the molded layer easily and securely such that it becomes relatively thinner at the outer edge part of the fine structure area than at the center part thereof.

In the surface-enhanced Raman scattering element in accordance with one aspect of the present invention, the fine structure part may be formed all over the principal surface of the substrate. This makes it possible to generate surface-enhanced Raman scattering all over the principal surface of the substrate.

The surface-enhanced Raman scattering element in accordance with one aspect of the present invention may further comprise a frame part formed on the principal surface of the substrate so as to surround at least the support part along the principal surface of the substrate. This can make the frame part protect the fine structure part, so as to improve reliability.

In the surface-enhanced Raman scattering element in accordance with one aspect of the present invention, the frame part may have a height from the principal surface of the substrate smaller than that of the fine structure part from the principal surface of the substrate. In this case, the relatively thin (low) frame part can be utilized as a region which sets a cut line for chipping.

Advantageous Effects of Invention

One aspect of the present invention can provide a surface-enhanced Raman scattering element which can stabilize surface-enhanced Raman scattering characteristics.

DESCRIPTION OF EMBODIMENTS

Figure 1:
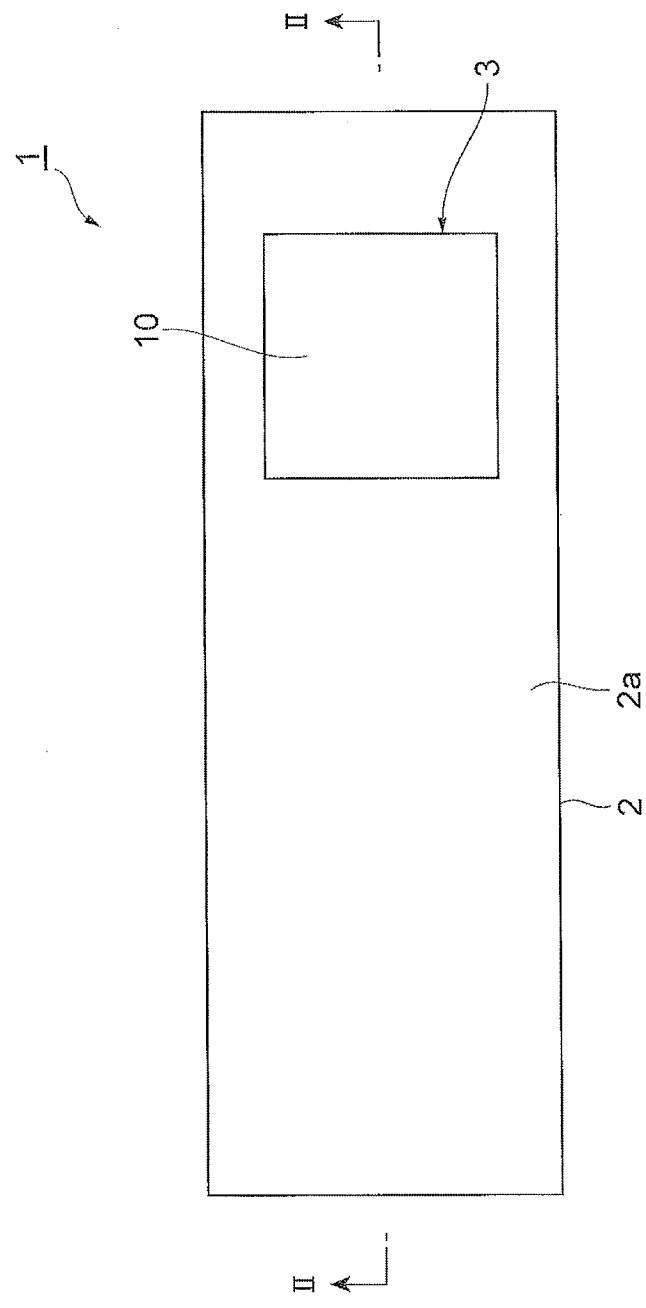
FIG. 1 is a plan view of the surface-enhanced Raman scattering unit in accordance with an embodiment of the present invention.

In the following, embodiments of the present invention will be explained in detail with reference to the drawings. In the drawings, the same or equivalent parts will be referred to with the same signs while omitting their overlapping descriptions.

Figure 2:
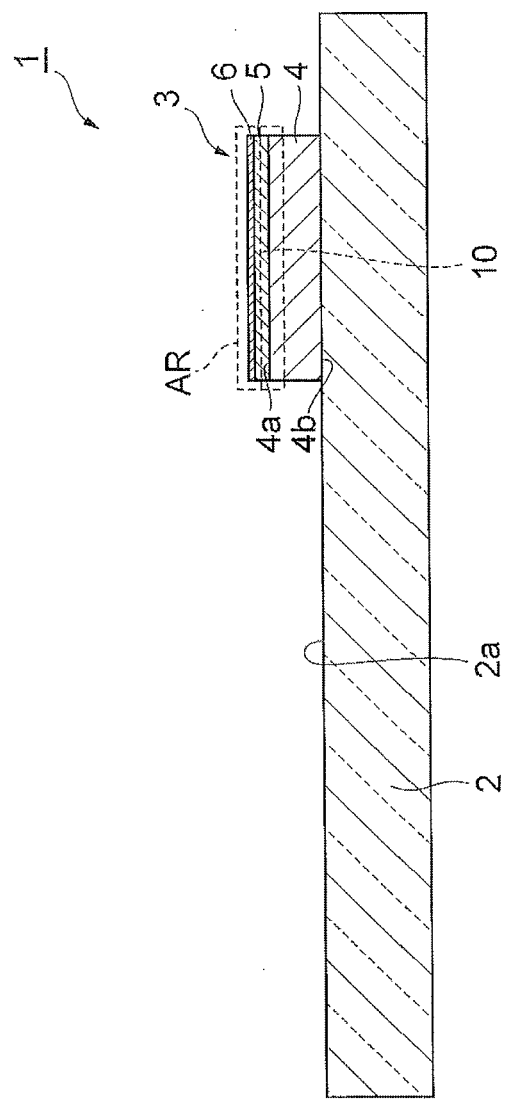
FIG. 2 is a sectional view taken along the line II-II of FIG. 1.

FIG. 1 is a plan view of the surface-enhanced Raman scattering unit in accordance with an embodiment, while FIG. 2 is a sectional view taken along the line of FIG. 1. As illustrated in FIGS. 1 and 2, a SERS unit (surface-enhanced Raman scattering unit) 1 in accordance with this embodiment comprises a handling board 2 and a SERS element (surface-enhanced Raman scattering element) 3 attached onto the handling board 2. The handling board 2 is a rectangular plate-shaped glass slide, resin board, ceramic board, or the like. The SERS element 3 is arranged on a front face 2a of the handling board 2 while being biased to one side in the longitudinal direction of the handling board 2.

The SERS element 3 comprises a substrate 4 attached onto the handling board 2, a molded layer 5 formed on a front face (principal surface) 4a of the substrate 4, and a conductor layer 6 formed on the molded layer 5. The substrate 4 is formed into a rectangular plate by silicon, glass, or the like and has an outer form on the order of several hundred μm×several hundred μm to several ten mm×several ten mm and a thickness on the order of 100 μm to 2 mm. A rear face 4b of the substrate 4 is secured to the front face 2a of the handling board 2 by direct bonding, bonding with a metal such as solder, eutectic bonding, fusion bonding by irradiation with laser light and the like, anodic bonding, or bonding with a resin.

Figure 3:
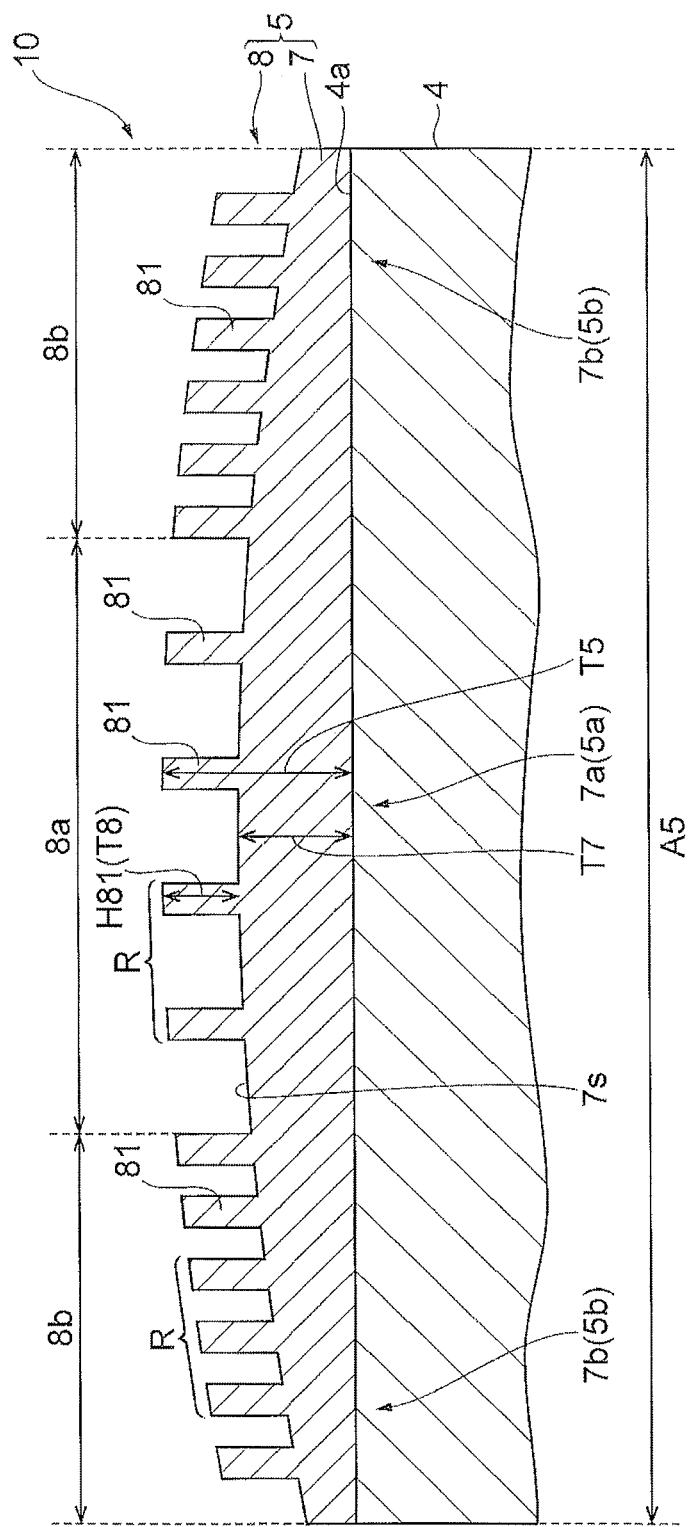
FIG. 3 is a schematic enlarged sectional view of a region AR in FIG. 2.

FIG. 3 is a schematic enlarged sectional view of a region AR in FIG. 2. FIG. 3 omits the conductor layer 6. As illustrated in FIG. 3, the molded layer 5 has a support part 7 formed on the front face 4a of the substrate 4 and a fine structure part 8 formed on the support part 7. The support part 7 is formed so as to extend all over the front face 4a of the substrate 4. The support 7 has a thickness T7 with such a gradient as to decrease gradually from a center part 7a of the support part 7 to an outer edge part 7b thereof. In other words, the thickness T7 of the support part 7 is relatively smaller at the outer edge part 7b than at the center part 7a. The thickness T7 of the support part 7 is about 200 nm at the center part 7a and about 100 nm at the outer edge part 7b, for example.

The fine structure part 8 is formed on the support 7 all over the front face 4a of the substrate 4. The fine structure part 8 is formed integrally with the support part 7. The molded layer 5 includes a fine structure area A5 formed with the fine structure part 8. Here, since the fine structure part 8 is formed all over the front face 4a of the substrate 4, the fine structure area A5 is also an area extending all over the front face 4a of the substrate 4. Since the support part 7 is also formed all over the front surface 4a of the substrate 4, the fine structure area A5 has a center part 5a and an outer edge part 5b which coincide with the center part 7a and outer edge part 7b of the support part 7, respectively.

The fine structure part 8 includes a plurality of projections 81 formed on the support 7. The projections 81 project from the support part 7 and are formed integrally with the support part 7. The projections 81 are arranged into a two-dimensional array on the support part 7 (i.e., on the front face 4a of the substrate 4). A surface 7s of the support part 7 is exposed between the projections 81 adjacent to each other. Each projection 81 is formed into a circular column, for example. The projections 81 may be arranged into a matrix, a triangle, a honeycomb, or the like. The form of the projection 81 is not limited to the circular column but may be any of columns, examples of which include elliptical columns and polygonal columns such as quadrangular columns, or any of cones.

The forming density of the projections 81 is relatively lower at the center part 5a of the fine structure area A5 than at the outer edge part 5b thereof. That is, the fine structure part 8 has a low-density region 8a which is a region including the center part 5a of the fine structure area A5 and exhibiting a relatively low forming density of the projections 81 and a high-density region 8b which is a region surrounding the low-density region 8a so as to include the outer edge part 5b of the fine structure area A5 and exhibiting a relatively high forming density of the projections 81.

Here, the forming density of the projections 81 is defined by the total volume of the projections 81 formed within a predetermined reference area R, for example. Therefore, the forming density herein becomes higher and lower when the total volume of the projections 81 formed within the predetermined area R is larger and smaller, respectively. Since the projections 81 to be compared with each other in terms of forming density have a uniform shape here, whether the forming density is high or low corresponds to whether the number of projections 81 formed within the predetermined area R is large or small.

The projections 81 are formed with a column diameter of about 120 nm, for example. The pitch of the projections 81 in the low-density region 8a is about 450 nm, for example. On the other hand, the pitch of the projections 81 in the high-density region 8b, an example of which is about 250 nm, is smaller than that in the low-density region 8a. The projections 81 have a height H81, an example of which is about 180 nm, which is substantially constant (i.e., have a uniform shape) in the low-density region 8a and high-density region 8b. That is, the fine structure part 8 has a thickness T8 which is substantially constant all over the fine structure area A5.

Since the thickness T8 of the fine structure part 8 is constant, while the thickness T7 of the support part 7 has a gradient, the total thickness T5 of the molded layer 5 has a gradient corresponding to the thickness T7 of the support part 7. More specifically, due to the gradient in the thickness T7 of the support part 7, the thickness T5 of the molded layer 5 is relatively smaller at the outer edge part 5b of the fine structure area A5 than at the center part 5a thereof. In other words, the thickness T5 of the molded layer 5 has such a gradient as to become smaller gradually from the center part 5a of the fine structure area A5 to the outer edge part 5b thereof according to the gradient in the thickness T7 of the support part 7.

The foregoing molded layer 5 is integrally formed by molding a resin (examples of which include resins based on acrylics, fluorine, epoxy, silicone, and urethane, PET, polycarbonate, and inorganic/organic hybrid materials) or low-melting glass arranged on the front face 4a of the substrate 4 by nanoimprinting, for example.

The conductor layer 6 is formed on the fine structure part 8. The conductor layer 6 reaches not only the surfaces of the projections 81 but also the surface 7s of the support part 7 exposed between the projections 81. Therefore, the conductor layer 6 has a fine structure corresponding to the fine structure part 8 of the molded layer 5. The conductor layer 6 has a thickness on the order of several nm to several μm, for example.

The conductor layer 6 like this is formed by vapor-depositing a conductor such as a metal (Au, Ag, Al, Cu, Pt, or the like) on the molded layer 5 molded by nanoimprinting, for example, as mentioned above. In the SERS element 3, the conductor layer 6 formed on the fine structure part 8 and the surface 7a of the support part 7 constructs an optical function part 10 which generates surface-enhanced Raman scattering.

A method for using the SERS unit 1 will now be explained. First, the SERS unit 1 is prepared. Subsequently, a sample of a solution (or a dispersion of a powder sample in a solution such as water or ethanol; the same hereinafter) is dropped with a pipette or the like, so as to be arranged on the optical function part 10. The sample is arranged on the conductor layer 6, which is formed on the surface 7s of the support part 7 and the surfaces of the projections 81 of the fine structure part 8. When dropping the solution sample, a spacer made of silicone or the like may be arranged beforehand on the handling board 2 in order to form a sample cell.

Next, when necessary for reducing the lens effect, a glass cover is mounted on the optical function part 10 (or can be mounted on a spacer when the spacer is used) and brought into close contact with the solution sample. Subsequently, the SERS unit 1 is set in a Raman spectroscopic analyzer, and the sample arranged on the optical function part 10 is irradiated with excitation light through the glass cover. This generates surface-enhanced Raman scattering at the interface between the optical function part 10 and sample, whereby surface-enhanced Raman scattering light derived from the sample is enhanced by about $10^8$ times, for example, and released. Hence, the Raman spectroscopic analyzer enables Raman spectroscopy with high sensitivity and high accuracy.

Not only the above-mentioned method, but the following methods may also be used for arranging the sample on the optical function part 10. For example, while holding the handling board 2, the SERS element 3 may be dipped in and lifted from the solution sample, and then the sample may be blown to dry. A minute amount of the solution sample may be dropped onto the optical function part 10 and left to dry. A powder sample may be dispersed as it is on the optical function part 10.

A method for manufacturing the SERS unit 1 will now be explained with reference to FIG. 4. First, as illustrated in (a) of FIG. 4, a mold M is prepared in this manufacturing method. The mold M has a pattern which is the reverse of the above-mentioned fine structure part 8 of the molded layer 5. More specifically, the mold M has a high-density region M8a at a center part formed with projections M81 having a relatively large column diameter and a low-density region M8b at an outer edge part formed with projections M82 having a relatively small column diameter.

In the mold M, a depression M83 defined by the projections M81, M82 adjacent to each other corresponds to the projection 81 in the molded layer 5. Since the projections 81 in the molded layer 5 have a fixed column diameter D81, the depressions M83 in the mold M have a fixed width. Therefore, in the high-density region M8a of the mold M formed with the relatively large projections M81, the depressions M83 have a wider gap therebetween and a relatively small total volume. In the low-density region M8b of the mold M formed with the relatively small projections M82, by contrast, the depressions M83 have a narrower gap therebetween and a relatively large total volume.

The mold M may be either a master mold for nanoimprinting or a replica mold formed by using the master mold. The mold M may be either a film mold made of PET, polycarbonate, PMMA, polyimide, silicone, or the like, or a silica mold, a nickel mold, a silicon mold, or the like without being restricted to film molds, for example.

Next, a wafer including the substrate 4 is prepared, and a nanoimprinting resin 50 is arranged on its surface 40a. As the nanoimprinting resin 50, a UV-curable resin (examples of which include resins based on acrylics, fluorine, epoxy, silicone, and urethane, PET, polycarbonate, and inorganic/organic hybrid materials) or low-melting glass can be used, for example.

Subsequently, as illustrated in (b) of FIG. 4, the mold M is pressed against nanoimprinting resin 50 on the wafer 40. As a consequence, each of the depressions M83 of the mold M is filled with the nanoimprinting resin 50 (though there is a case where it is not fully filled). At this time, the depressions M83 in the high-density region M8a of the mold M where the total volume of the depressions M83 is relatively small can be filled with a smaller amount of resin. By contrast, a relatively large amount of resin is necessary for filling the depressions M83 in the low-density region M8b of the mold M where the total volume of the depressions M83 is relatively large.

When the molded layer 5 is formed by transferring the pattern of the mold M to the nanoimprinting resin 50 under such a circumstance, relatively small and large amounts of resin are required to fill the depressions M83 in the high-density region M8a and low-density region M8b, respectively, at the time of pressing the mold M against the nanoimprinting resin 50, whereby a gradient is generated in the amount of resin utilized for forming the support part 7 so as to correspond to these regions M8a, M8b, which results in the above-mentioned gradient in thickness of the support part 7. Thereafter, the nanoimprinting resin 50 is cured by UV irradiation, for example, and the mold M is released from the molded layer 5 as illustrated in (c) of FIG. 4.

Thus setting the low-density region 8a and high-density region 8b in the fine structure part 8 can easily and securely form the molded layer 5 (support part 7) having a gradient in thickness because of the fact that the amount of resin required for forming the depressions 81 in the high-density region 8b (the amount of resin for filling the depressions M83 in the low-density region M8b of the mold M) is greater than the amount of resin required for forming the depressions 81 in the low-density region 8a (the amount of resin for filling the depressions M83 in the high-density region M8a of the mold M).

Figure 4:
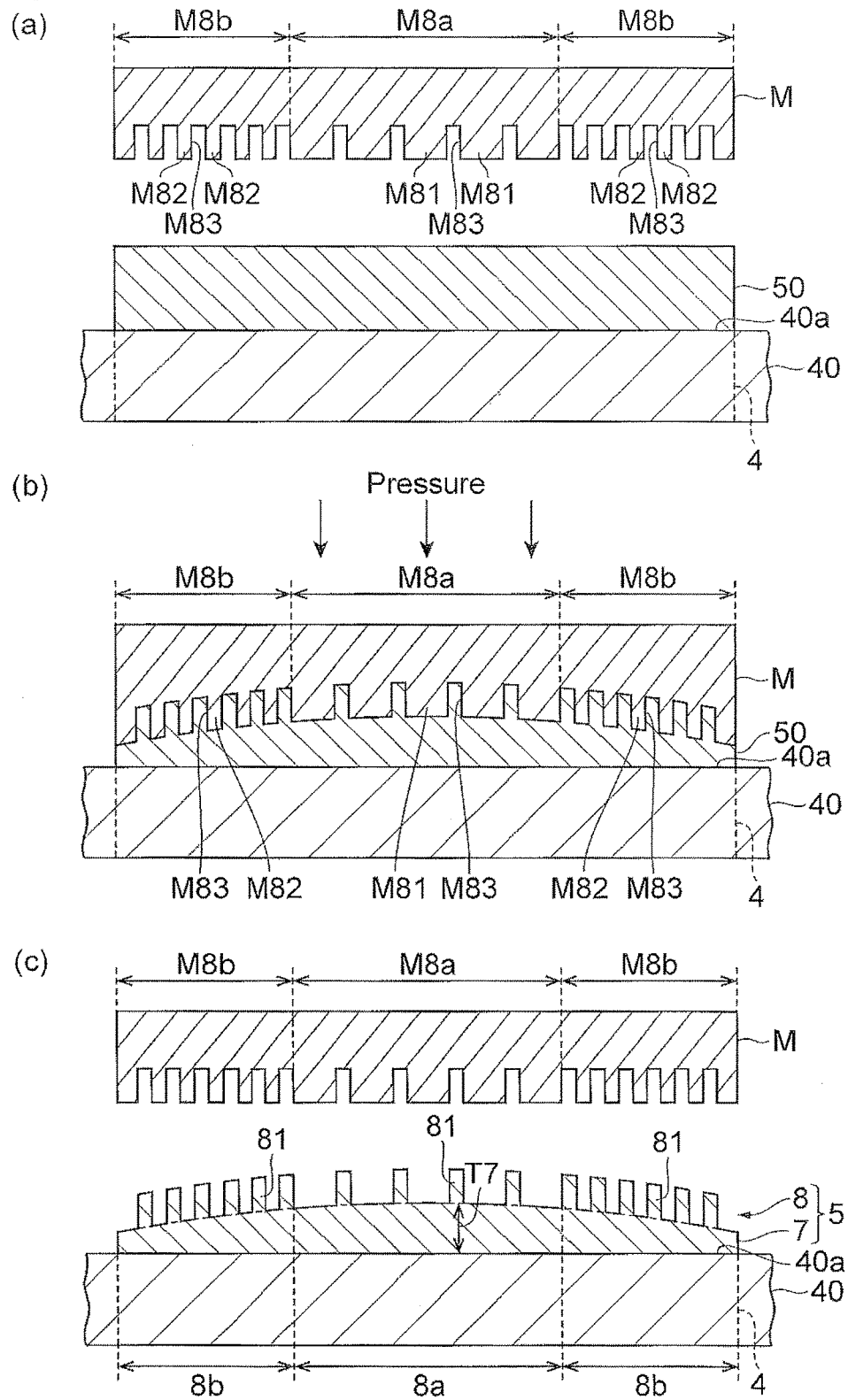
FIG. 4 is a diagram illustrating main steps of a method for manufacturing the surface-enhanced Raman scattering unit depicted in FIG. 1.

Here, the nanoimprinting process illustrated in (a) to (c) of FIG. 4 may be performed such as to form a plurality of molded layers 5 collectively on a wafer level by using the mold M in a wafer size, or a plurality of molded layers 5 may be formed sequentially by repeatedly using the mold M having a size smaller than that of the wafer (step & repeat).

Thereafter, a conductor such as a metal (Au, Ag, Al, Cu, Pt, or the like) is vapor-deposited on the molded layer 5 (fine structure part 8), so as to form the conductor layer 6, thereby constituting the optical function part 10. This constructs the SERS element 3. Then, the wafer 40 is diced into the SERS elements 3, and the cut SERS element 3 is secured to the handling board 2, whereby the SERS unit 1 is obtained.

In the SERS element 3 in accordance with this embodiment, as explained in the foregoing, the molded layer 5 has the fine structure part 8, on which the conductor layer 6 is formed, so as to construct the optical function part 10 for generating surface-enhanced Raman scattering. In particular in this SERS element 3, the thickness of the molded layer 5 is constructed relatively large at the center part 5a of the fine structure area A5 formed with the fine structure part 8 but relatively small at the outer edge part 5b.

Therefore, when releasing the mold M from the molded layer 5 in order to form the molded layer 5 by nanoimprinting, the fine structure part 8 is more likely to comply with the release of the replica mold at the outer edge part 5b of the fine structure area A5 and keep its form at the center part 5a of the fine structure area A5. This inhibits the fine structure part 8 (projections 81) from being damaged and thus can stabilize surface-enhanced Raman scattering characteristics.

In the SERS element 3 in accordance with this embodiment, the thickness T5 of the molded layer 5 is relatively thin at the outer edge part 5b of the fine structure area A5 (the outer edge part of the molded layer 5 here), whereby the outer edge part 5b can be utilized as a region for setting a cut line for chipping and is less likely to peel at the time of dicing for chipping.

In the SERS element 3 in accordance with this embodiment, the fine structure part 8 includes a plurality of projections 81, while the forming density of the projections 81 is relatively lower at the center part 5a of the fine structure area A5 than at the outer edge part 5b thereof. The molded layer 5 like this can be formed easily and securely such that its thickness T5 is relatively smaller at the outer edge part 5b of the fine structure area A5 than at the center part 5a thereof by nanoimprinting using the above-mentioned mold M, for example. The same also applies when providing the thickness T7 of the support part 7 with the above-mentioned gradient.

In the SERS element 3, the molded layer 5 has the support part 7 extending along the front face 4a of the substrate 4, while the fine structure part 8 (projection 81) is constructed integrally with the support part 7. This restrains the fine structure part 8 from peeling (the projections 81 from falling and dropping) and thus improves reliability.

The foregoing embodiment explains one embodiment of the surface-enhanced Raman scattering element. Therefore, the present invention is not limited to the above-mentioned SERS element 3, but may encompass any modifications of the SERS element 3 within the scope not altering the gist of each claim.

Figure 5:
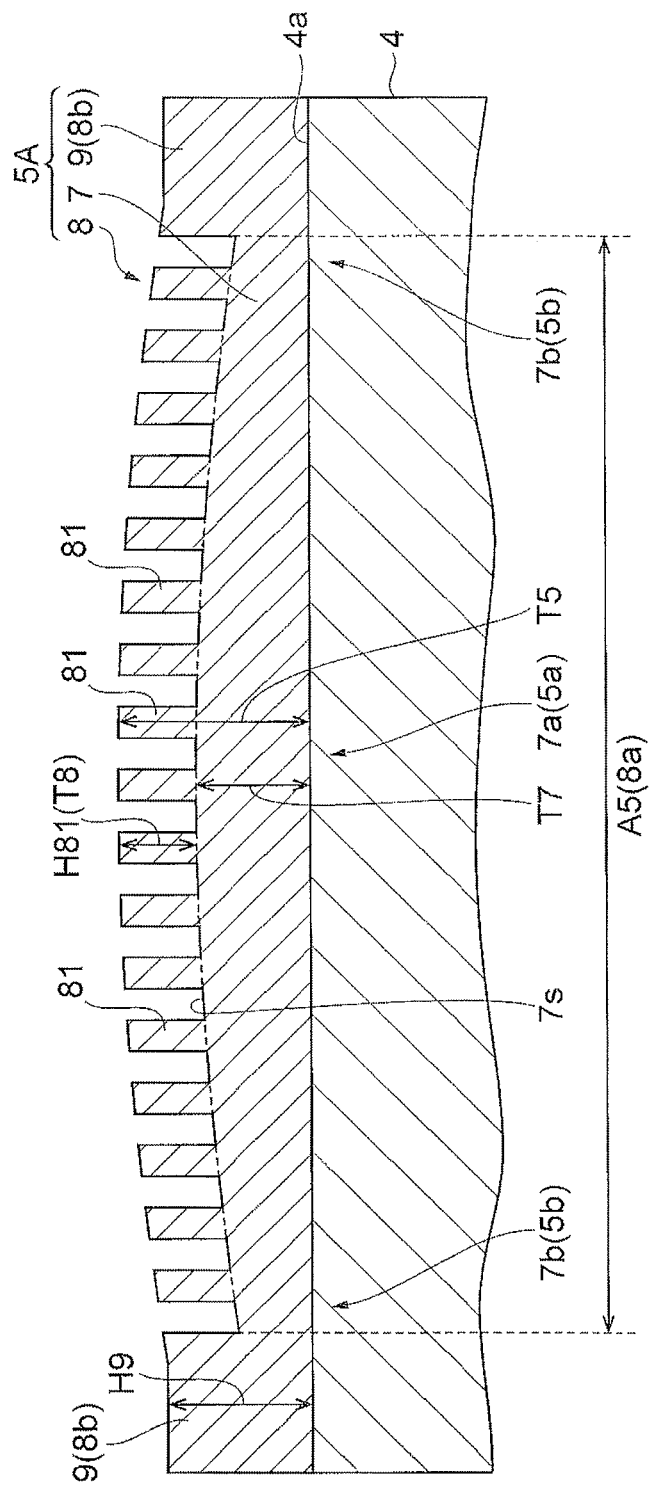
FIG. 5 is an enlarged sectional view illustrating a modified example of a molded layer depicted in FIG. 3.

For example, the SERS element 3 may comprise a molded layer 5A illustrated in FIG. 5 in place of the above-mentioned molded layer 5. In the molded layer 5A, the support part 7 and fine structure part 8 are formed at the center part of the front face 4a of the substrate 4. Therefore, the fine structure area A5 of the molded layer 5A does not cover all over the front face 4a of the substrate 4 but only the center part thereof.

The thickness T8 of the fine structure part 8 is constant, while the thickness T7 of the support part 7 has a gradient, whereby the thickness T5 of the molded layer 5A has a gradient corresponding to the thickness T7 of the support part 7 in this case as well. More specifically, due to the gradient in the thickness T7 of the support part 7, the thickness T5 of the molded layer 5A is relatively smaller at the outer edge part 5b of the fine structure area A5 than at the center part 5a thereof. In other words, the thickness T5 of the molded layer 5A has such a gradient as to become smaller gradually from the center part 5a of the fine structure area A5 to the outer edge part 5b thereof according to the gradient in the thickness T7 of the support part 7.

The molded layer 5A further has a frame part 9 formed on the front face 4a of the substrate 4. The frame part 9 is continuous from the support part 7 and formed integrally therewith. The frame part 9 is arranged at an outer peripheral part of the front face 4a of the substrate 4 and formed like a ring so as to surround a part of the fine structure part 8 on the support part 7 side and the support part 7 along the front face 4a of the substrate 4. The frame part 9 has a height H9 from the front face 4a of the substrate 4 smaller than the height of the fine structure part 8 from the front face 4a of the substrate 4 (the sum of the thickness T7 of the support part 7 and the thickness T8 of the fine structure part 8).

Thus providing the outer peripheral part of the substrate 4 with the frame part 9 protects the fine structure part 8, thereby improving reliability. The frame part 9 can also be used as a space for providing an alignment mark for mounting, a space to be marked for identifying chips, and a region for setting a cut line for chipping. Chipping, if any, occurring in the SERS element 3 stops at the frame part 9, thereby avoiding an effective area including the fine structure part 8 from being damaged.

In the molded layer 5A, the forming density of the projections 81 is constant in the fine structure area A5, but the frame part 9 can be regarded as a relatively large single projection, whereby the frame part 9 functions as the high-density region 8b (i.e., the fine structure area A5 as a whole functions as the low-density region 5a). Hence, as in the case of forming the molded layer 5, preparing the mold M for the molded layer 5A and pressing it against the nanoimprinting resin 50 necessitates a large amount of resin for forming the frame part 9. As a result, a part of the resin for forming the support part 7 is utilized for forming the frame part 9, whereby the support part 7 can be provided with a gradient.

Figure 6:
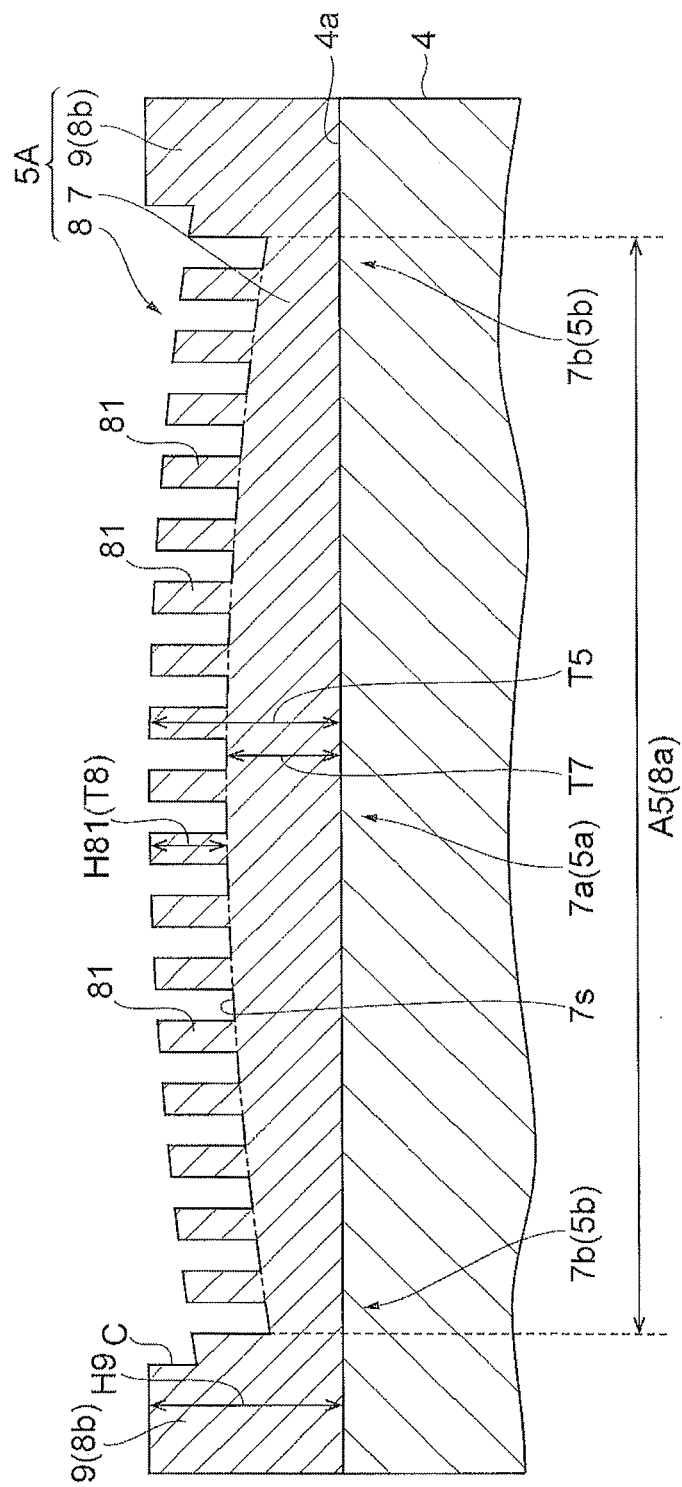
FIG. 6 is an enlarged sectional view illustrating a modified example of the molded layer depicted in FIG. 5.

In the molded layer 5A, as illustrated in FIG. 6, the height H9 of the frame part 9 may be greater than the height of the fine structure part 8 (the sum of the thickness T7 of the support part 7 and the thickness T8 of the fine structure part 8), so that the frame part 9 surrounds the support part 7 and fine structure part 8. In this case, the frame part 9 and support part 7 form a recess C, whose bottom face (the surface 7s of the support 7) is formed with the fine structure part 8. Therefore, the fine structure part 8 is protected securely. Setting the frame part 9 higher can mitigate distortions caused by the difference in thermal expansion between the substrate 4 and molded layer 5, thereby preventing the molded layer 5 from peeling and so forth due to temperature cycles and the like.

The recess C can also reserve the solution sample, thereby improving the ratio by which the sample adheres to the fine structure part 8 (i.e., to the conductor layer 6 on the fine structure part 8). Raman spectroscopic analysis can be conducted with a glass cover mounted on the frame part 9 and thus can be performed while protecting the fine structure part 8 (blocking impurities from mingling) and preventing the solution from evaporating. The distance between the arranged glass cover and the fine structure part 8 can be kept constant among different elements, so as to achieve stable measurement (suppress fluctuations in measurement caused by variations in distance). Arranging a flat glass cover can suppress the lens effect of the solution sample, thereby enabling appropriate measurement.

Figure 7:
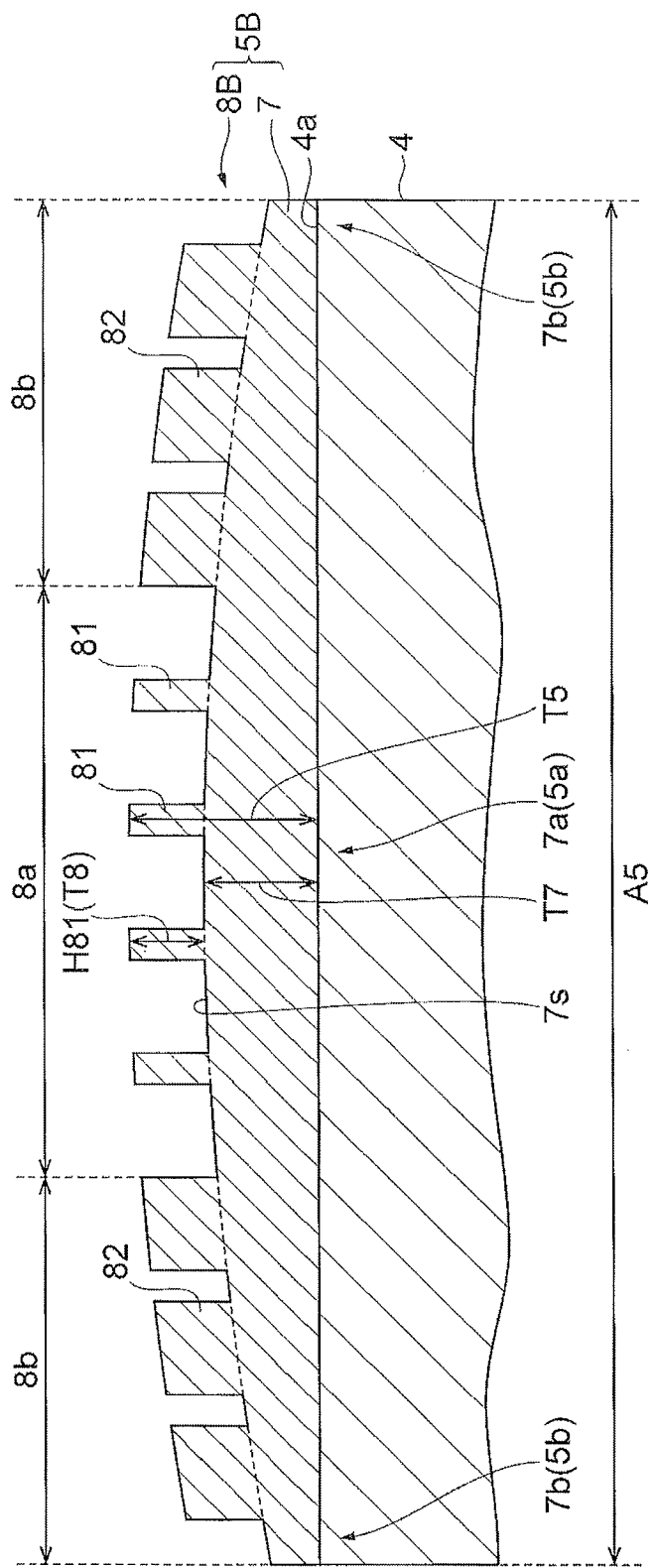
FIG. 7 is an enlarged sectional view illustrating a modified example of the molded layer depicted in FIG. 3.

Here, the SERS element 3 may comprise a molded layer 5B illustrated in FIG. 7 in place of the molded layer 5. The molded layer 5B has a fine structure part 8B instead of the fine structure part 8. The fine structure part 8B is formed all over the front face 4a of the substrate 4, whereby the fine structure area A5 extends all over the front face 4a of the substrate 4. The fine structure part 8B has a plurality of projections 81, 82 projecting from the support part 7.

The projections 81 have a column diameter smaller than that of the projections 82 and are formed at the center part 5a of the fine structure area A5. The projections 82 are formed at the outer edge part 5b of the fine structure area A5. The space between the projections 81 adjacent to each other is greater than that between the projections 82 adjacent to each other. Therefore, the forming density of the projections 81 is lower than that of the projections 82. In other words, as with the fine structure part 8, the fine structure part 8B has a low-density region 8a which is a region including the center part 5a of the fine structure area A5 and exhibiting a relatively low forming density of the projections 81 and has a high-density region 8b which is a region surrounding the low-density region 8a so as to include the outer edge part 5b of the fine structure area A5 and exhibiting a relatively high forming density of the projections 82.

Since the thickness T8 of the fine structure part 8B is constant, while the thickness T7 of the support part 7 has a gradient, the total thickness T5 of the molded layer 5B also has a gradient corresponding to the thickness T7 of the support part 7. More specifically, due to the gradient in the thickness T7 of the support part 7, the thickness T5 of the molded layer 5B is relatively smaller at the outer edge part 5b of the fine structure area A5 than at the center part 5a thereof. In other words, the thickness T5 of the molded layer 5A has such a gradient as to become smaller gradually from the center part 5a of the fine structure area A5 to the outer edge part 5b thereof according to the gradient in the thickness T7 of the support part 7.

Thus, the form (column diameter) of projections may vary between the low-density region 8a and high-density region 8b of the fine structure part 8B. Preparing the mold M for the molded layer 5B and pressing it against the nanoimprinting resin 50 can provide the support part 7 with a gradient due to the fact that a larger amount of resin is necessary for forming the projections 82 than the projections 81 in this case as well.

The molded layer 5 includes the fine structure part 8 having the low-density region 8a and high-density region 8b whose forming densities of the projections 81 differ from each other, so that the thickness T5 of the molded layer 5 (the thickness T7 of the support part 7) is provided with a gradient due to whether the forming density of the projections 81 is high or low (due to whether the required amount of resin is large or small), when forming the molded layer 5 by nanoimprinting in the above-mentioned embodiment, but the method for providing the thickness T5 of the molded layer 5 with a gradient is not limited thereto.

Figure 8:
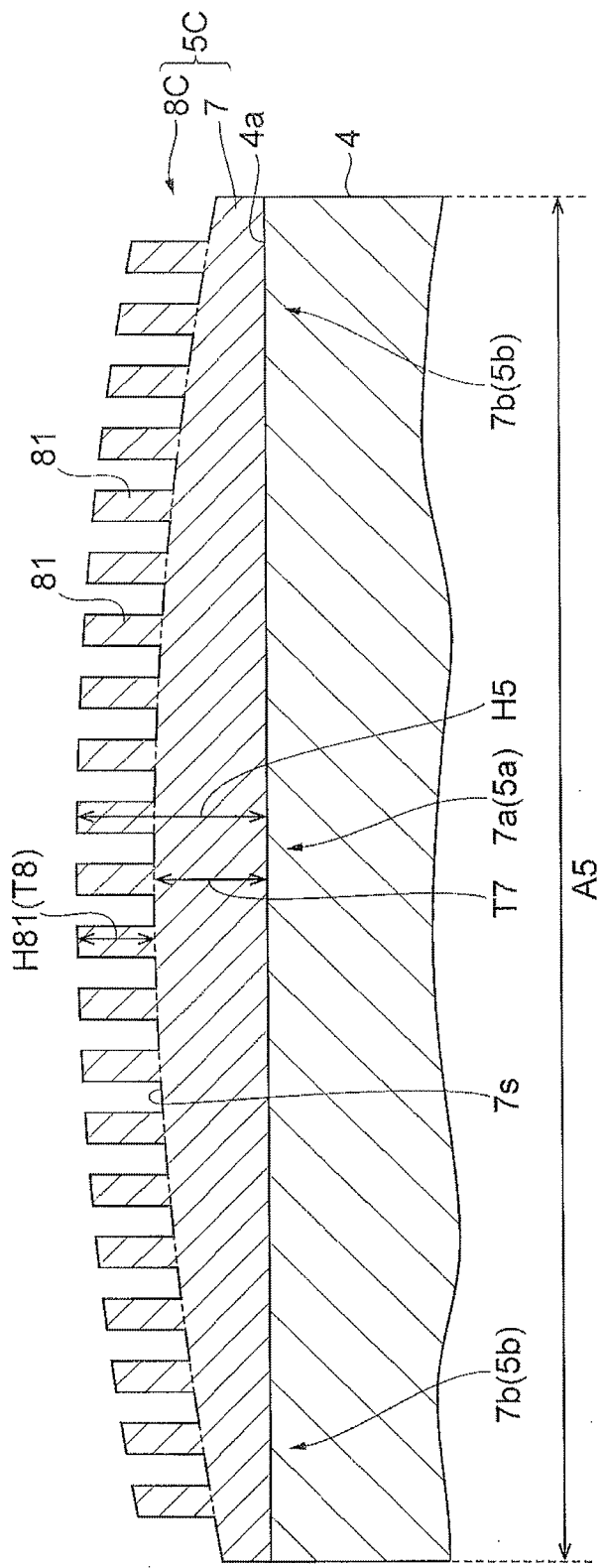
FIG. 8 is an enlarged sectional view illustrating a modified example of the molded layer depicted in FIG. 3.
Figure 9:
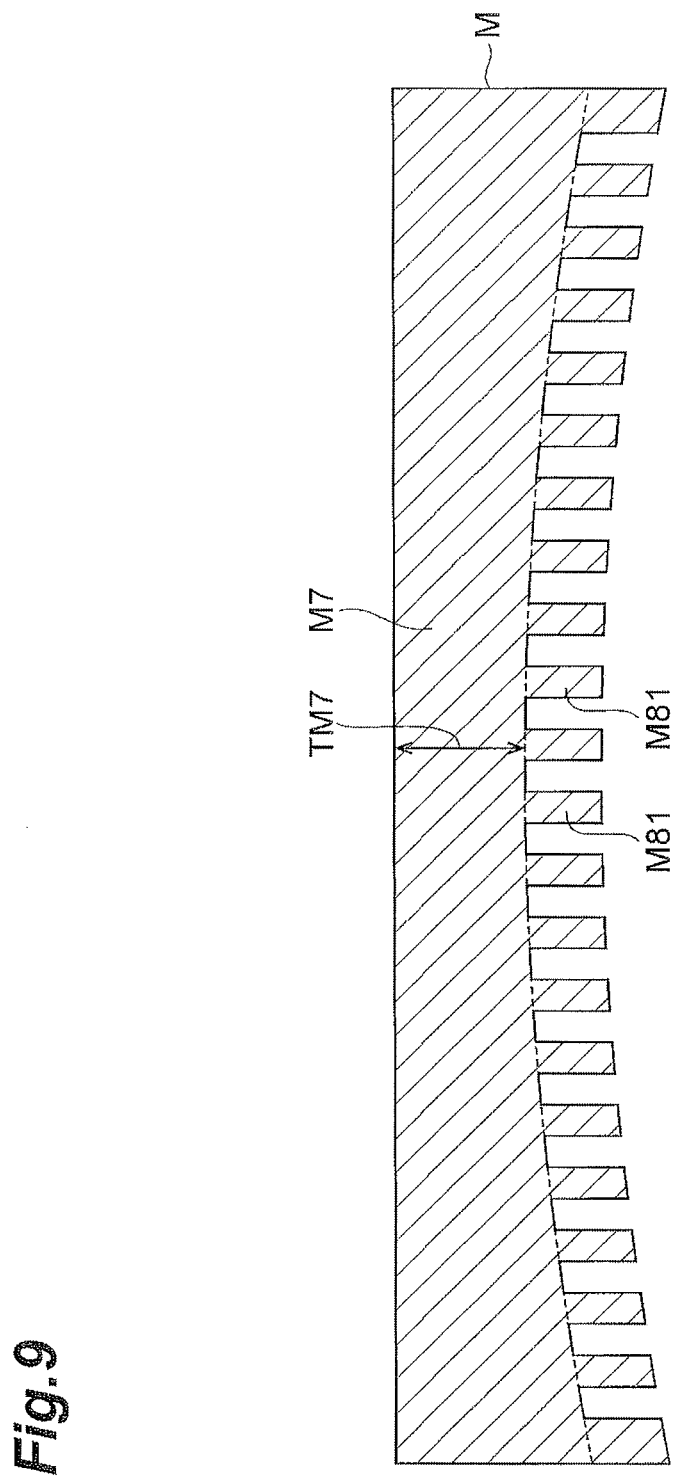
FIG. 9 is a sectional view illustrating a mold for forming the molded layer depicted in FIG. 8.

That is, even when a molded layer 5C includes a fine structure part 8C exhibiting a uniform forming density of the projections 81 as illustrated in FIG. 8, the thickness T5 of the molded layer 5C (i.e., the thickness T7 of the support part 7) can be provided with such a gradient as to become smaller gradually from the center part 5a of the fine structure area A5 to the outer edge part 5b by similar nanoimprinting if the mold M used for forming this layer has a thickness TM7 of a support part M7 provided with a corresponding gradient beforehand as illustrated in FIG. 9.

Further, the molded layer in the SERS element 3 is only required to be relatively thinner at the outer edge part 5b of the fine structure area A5 formed with the fine structure part 8 than at the center part 5a thereof, but may become thinner stepwise (e.g., in two or three steps) from the center part 5a to the outer edge part 5b and need not be formed by nanoimprinting.

While the forming density of the projections 81 in the fine structure part 8 has two stages of high and low densities in the molded layer 5, the forming density of the projections 81 is only required to be relatively lower at the center part 5a of the fine structure area A5 than at the outer edge part 5b thereof and may be provided with three or more stages of forming density differences.

The conductor layer 6 is not limited to the one directly formed on the molded layer 5 (fine structure part 8), but may be formed indirectly on the molded layer 5 (fine structure part 8) with a layer such as a buffer metal (Ti, Cr, or the like) for improving the adhesion of a metal to the molded layer 5 (fine structure part 8), for example, interposed therebetween.

Without being restricted to those mentioned above, various materials and forms can be employed for the above-mentioned constituents of the SERS element 3.

Figure 10:
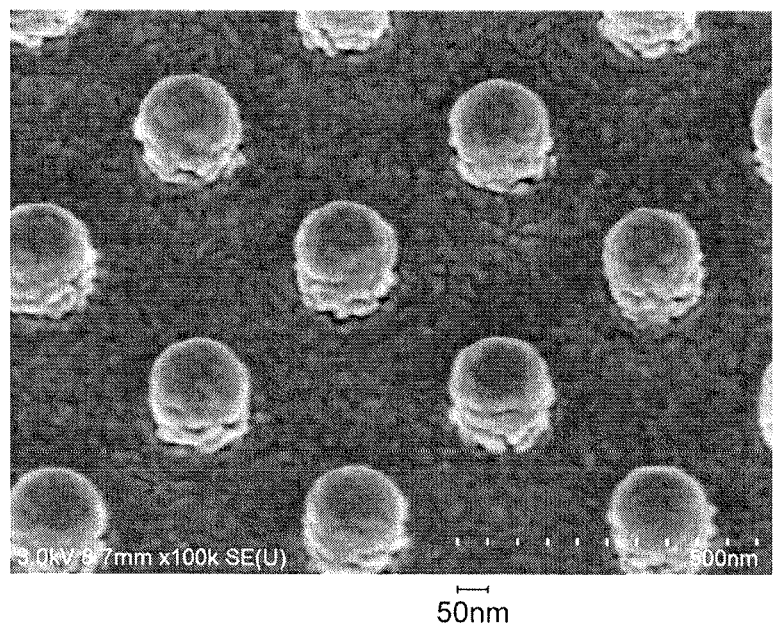
FIG. 10 is a photograph of an optical function part of a surface-enhanced Raman scattering unit.

The optical function part shown in FIG. 10 is one in which Au was vapor-deposited as a conductor layer so as to yield a thickness of 50 nm in a fine structure part made of a nanoimprinting resin having a plurality of pillars (each having a diameter of 120 nm and a height of 180 nm) periodically arranged at a predetermined pitch (center line distance of 360 nm).

INDUSTRIAL APPLICABILITY

One aspect of the present invention can provide a surface-enhanced Raman scattering element which can stabilize surface-enhanced Raman scattering characteristics.

REFERENCE SIGNS LIST

1: SERS unit (surface-enhanced Raman scattering unit); 3: SERS element (surface-enhanced Raman scattering element); 4: substrate; 4a: front face (principal surface); 5: molded layer; 5a: center part; 5b: outer edge part; 6: conductor layer; 7: support part; 8: fine structure part; 9: frame part; 10: optical function part; 81: projection; A5: fine structure area.

The invention claimed is:

1. A surface-enhanced Raman scattering element comprising:
a substrate having a principal surface;
a molded layer having a support part formed on the principal surface of the substrate so as to extend along the principal surface and a fine structure part formed on the support part; and
a conductor layer formed on the fine structure part and constituting an optical functional part for generating surface-enhanced Raman scattering;
wherein the molded layer is relatively thinner in a direction intersecting the principal surface of the substrate at an outer edge part of a fine structure area formed with the fine structure part in the molded layer than at a center part of the fine structure area,
the fine structure part is formed integrally with the support part, and consists of projections arranged into a two-dimensional array on the support part, and
the thickness of the molded layer in a projection formed in the center part of the fine structure area is greater than the thickness of the molded layer in a projection formed in the outer edge part of the fine structure area.

2. A surface-enhanced Raman scattering element according to claim 1,
wherein the projections have a forming density relatively lower at the center part of the fine structure area than at the outer edge part thereof.

3. A surface-enhanced Raman scattering element according to claim 1, wherein the molded layer is made relatively thinner in the direction intersecting the principal surface of the substrate at the outer edge part of the fine structure area than at the center part of the fine structure area due to a gradient in thickness of the support part.

4. A surface-enhanced Raman scattering element according to claim 1, wherein the fine structure part is formed all over the principal surface of the substrate.

5. A surface-enhanced Raman scattering element according to claim 1, further comprising a frame part formed on the principal surface of the substrate so as to surround at least the support part along the principal surface of the substrate.

6. A surface-enhanced Raman scattering element according to claim 5, wherein the frame part has a height from the principal surface of the substrate smaller than that of the fine structure part from the principal surface of the substrate.

* * * * *